United States Patent [19]

Sacks

[11] 4,426,335

[45] Jan. 17, 1984

[54] PROCESS FOR MAKING PHOSPHORUS DERIVATIVES OF AMINOTHIOMETHYLCARBAMATES

[75] Inventor: Clifford E. Sacks, Portage, Mich.

[73] Assignee: The Upjohn Company, Kalamazoo, Mich.

[21] Appl. No.: 378,156

[22] Filed: May 14, 1982

Related U.S. Application Data

[63] Continuation of Ser. No. 181,611, Sep. 5, 1980, abandoned, which is a continuation-in-part of Ser. No. 151,557, May 20, 1980, abandoned.

[51] Int. Cl.$^3$ .............................................. C07F 9/24
[52] U.S. Cl. ...................................... 260/968; 549/5; 549/220; 260/936; 260/937
[58] Field of Search ..................... 260/968, 961; 549/5, 549/220

[56] References Cited

U.S. PATENT DOCUMENTS 4,024,277  5/1977  Engel .................................. 424/285
4,081,536  3/1978  Nelson ............................... 260/938

OTHER PUBLICATIONS

Kuhle, "Synthesis", No. 11, 11/1970, pp. 561–580.
Alimov et al, "Translation of Izvestiya Akademii Nauk, Otdelenie Khimicheskikh" Nauk, No. 6, 6/1963, pp. 1132–1134, pp. 1034 to 1036.

Primary Examiner—Anton H. Sutto
Attorney, Agent, or Firm—Joan Thierstein

[57] ABSTRACT

This invention pertains to novel processes for preparing phosphorus derivatives of aminothiomethylcarbamates known to be useful as pesticides. The processes use products prepared by a novel method which reacts disulfides of various amides of phosphoric acids with chlorine or bromine. Such sulfenyl halide products are advantageous and obtained in unexpected yields. Therefore, the method is also unobvious. When the novel sulfenyl bromides of this invention are intermediates unexpected yields of pesticides are obtained.

22 Claims, No Drawings

PROCESS FOR MAKING PHOSPHORUS DERIVATIVES OF AMINOTHIOMETHYLCARBAMATES

This is a continuation of application Ser. No. 181,611 filed Sept. 5, 1980 which is a continuation-in-part of Ser. No. 151,557 filed May 20, 1980 both now abandoned.

DESCRIPTION

BRIEF SUMMARY OF THE INVENTION

This invention pertains to novel processes for preparing phosphorus derivatives of aminothiomethylcarbamates. These carbamates are known to be useful as pesticides. The invention is particularly directed to the use of a product which is prepared by a reaction of a disulfide of various amides of phosphoric acids with chlorine or bromine. The product includes previously shown sulfenyl chlorides of various amides of phosphoric acids for use as intermediates in a process to make the pesticides. The reaction preparing the sulfenyl chloride or bromide product for use herein is novel. Further, the preparation of sulfenyl chlorides or bromides according to the instant case is unexpectedly advantageous and therefore unobvious over the prior art. Finally, the disulfides of the invention include selected compounds which insofar as is presently known, no one has previously prepared.

BACKGROUND OF THE INVENTION

N-[(phosphinyl)amino]thio- and N-[(phosphinothioyl)amino]thiomethylcarbamates, a process for preparation and formulations of them suitable for pesticidal use are shown in U.S. Pat. No. 4,081,536, issued Mar. 28, 1978. Phosphoroaminosulfenyl derivatives of benzofuran carbamates and preparation thereof are disclosed in U.S. Pat. No. 4,024,277, issued Mar. 17, 1977. Additional N-[(phosphinyl or phosphinothioyl)amino]thiomethylcarbamates and pesticidal methods for use thereof are disclosed in U.S. application Ser. No. 962,266, filed Nov. 20, 1978. These phosphorus acid derivatives of aminothiomethylcarbamate pesticides are among the compounds prepared by the novel processes of the present invention and, therefore, the above patents and application can be referred to for relevant status of the art.

Other prior art includes a review of E. Kühle, "One Hundred Years of Sulfenic Acid Chemistry I. Sulfenyl Halide Syntheses", Synthesis International Journal of Methods in Synthetic Organic Chemistry, No. 11, pp. 561-580 (November, 1970) and a disulfide preparation by M. V. Kalnins, "Reactions of Phthalimide and Potassium Phthalimide with Sulfur Monochloride", Can. J. Of Chem. Vol. 44, pp, 2111-2113 (1966). Although the review discloses numerous sulfenyl halides prepared by halogenation of organic disulfide, no compounds containing the phosphorus nitrogen sulfur linkage of the present invention are shown. Likewise, although Kalnins' discloses disulfides, the P—N—S linkage is not shown. The references P. I. Alimov, et al., "Derivatives of Diethoxyphosphorylamido-N-Sulfenic Acid", Bulletin of the Academy of Sciences of the USSR, Division of Chemical Science, English Edition, pp. 1220-1221 (1964), translated from Izvestiya Akademii Nauk SSSR, Seriya Khimicheskaya No. 7, pp. 1316-1317 (July, 1964) and P. I. Alimov, et al., "Synthesis of Some N-Sulfene Derivatives of the Amide of Diethylphosphoric Acid", Bulletin of the Academy of Science of the USSR, Division of Chemical Science, English Edition, pp. 1034-1036 (1964), translated from Izvestiya Akedemii Nauk, Otdelenie Khimicheskikh Nauk, No. 6, pp. 1132-1134 (June 1963) are also relevant. These references show the preparation of N-(sulfenechloro)ethylamide of diethylphosphoric acid and its reaction with simple amines and alcohols. However, contrary to the present invention the preparation is accomplished by the action of sulfuryl chloride on a disulfide precursor. A similar preparation using sulfuryl chloride is shown in U.S. Pat. No. 4,024,277 cited above.

The Alimov, et al, references disclose a limited number of disulfide species. Further, U.S. Pat. No. 4,024,277 shows a process which appears to prepare additional disulfides. However, selected disulfides of the present invention are novel compounds not taught by these references.

Further background teaching phosphoramide reactants denoted as Formula VI herein is found in Methoden der Organischen Chemie (Houben-Weyl) Volume 12, part 2, pages 610, 760 (thiophosphoramides) and pages 276, 413 (phosphoramides) George Thieme Verlag (Pub.), Stutgart, Germany, 1963. In addition, L. Anschiitz, et al. Ber. 61, 1264 (1928) teaches a benzothiophosphol chloride from which the corresponding amides of this invention can be made.

DETAILED DESCRIPTION OF THE INVENTION

The present invention is a process for preparing compounds having the formula

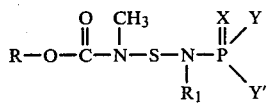

I wherein R is selected from the group consisting of

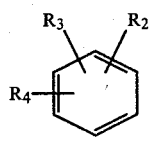

a.

wherein $R_2$, $R_3$ and $R_4$ are the same or different and are selected from the group consisting of hydrogen, lower alkyl of one to five carbon atoms, inclusive, halogen, lower alkoxy of one to five carbon atoms, inclusive, lower alkylthio of one to five carbon atoms, inclusive, dialkylamino with each alkyl the same or different and having one to three carbon atoms, inclusive, and $N=CHN(CH_3)_2$;

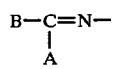

b.

wherein A and B are the same or different and are selected from the group consisting of lower alkyl of one to five carbon atoms, inclusive, lower alkylthio of one to five carbon atoms, inclusive, phenylthio wherein phenyl is unsubstituted or substituted with one to three substituents, same or different, selected from the group consisting of halogen and lower alkyl of one to four carbon atoms, inclusive, monocyano substituted alkylthio of one to five carbon atoms, inclusive, cyano, alkoxy having one to five carbon atoms, inclusive, phenyl, and hydrogen, with the proviso that when A is hydrogen, B is of the formula:

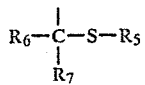

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula:

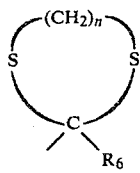

wherein n is 2 or 3 and the alkylene portion of the ring is unsubstituted or substituted with one or two methyl groups; A and B taken together with the carbon atom to which they are attached form a dithio heterocyclic of the formula:

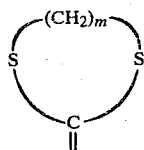

wherein m is 2 or 3 and the alkylene portion of the ring is unsubstituted or substituted with one to two methyl groups, and

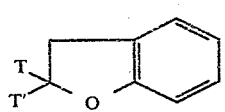

wherein T and T' can be the same or different and are selected from the group consisting of hydrogen and lower alkyl of from one to six carbons; $R_1$ is selected from the group consisting of lower alkyl, phenyl, substituted phenyl, phenyl lower akyl, and cycloalkyl; X is oxygen or sulfur; Y and Y' are the same or different and are selected from the group consisting of $Y_1$ and $Y_1'$       $I_1$ and Y and Y' taken together to form a functionality selected from the group consisting of:

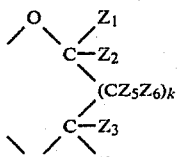     I'

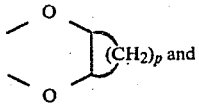     I''

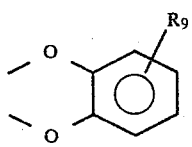     I''' wherein $Y_1$ and $Y_1'$ are selected from the group consisting of lower alkyl, lower alkoxy, lower alkylthio, cycloalkyl, phenyl, substituted phenyl, phenoxy, substituted phenoxy, thiophenoxy, and substituted thiophenoxy; $Z_1$ through $Z_6$ are the same or different and are selected from the group consisting of hydrogen, methyl and ethyl; and k is 0 or 1, p is three or four and $R_9$ is selected from the group consisting of hydrogen, lower alkyl, lower alkoxy and halogen; which comprises:

step 1: reacting a compound having the formula

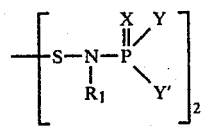     V wherein $R_1$, X, Y, and Y' are as defined above with chlorine or bromine and step 2: reacting the product of the step 1 reaction with a compound having the formula $ROC(O)N(CH_3)H$ wherein R is the same as above.

Compounds of formula V above are referred to herein as disulfides. The disulfides useful in the present invention include selected compounds which are novel. These compounds have the formula

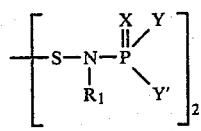     V' wherein $R_1$ and X are as defined above, and Y and Y' are limited to substituents wherein Y and Y' are taken together to form a functionality selected from the group consisting of

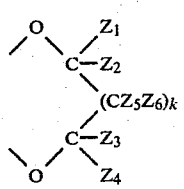     I'

-continued

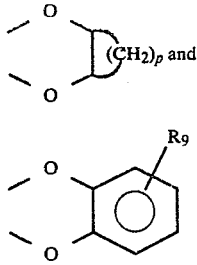
I''

I''' wherein $Z_1$ through $Z_6$, k, p. and $R_9$ are as described above. None of the above cited prior art references teach the novel disulfides of the present invention.

In the foregoing designation of variables, "lower alkoxy" means methoxy, ethoxy, propoxy, isopropoxy, butoxy, pentoxy, and the further isomeric forms thereof. Likewise, "lower alkylthio" means methylthio, ethylthio, propylthio, isopropylthio, butylthio, pentylthio, and further isomeric forms thereof.

"Lower alkyl" means methyl, ethyl, propyl, butyl, pentyl, and the isomeric forms thereof; while "cycloalkyl" means cyclopropyl, cyclobutyl, cyclopentyl, cyclohexyl optionally substituted with methyl, ethyl and propyl to a total of nine carbon atoms.

"Phenlower alkyl" means benzyl, phenethyl, phenpropyl, phenbutyl, phenpentyl and isomeric forms thereof.

"Substituted phenyl" means lower alkyl, lower alkoxy, halogen, nitro, and cyano-substituted-phenyl. There can be combinations of substituents such as 4-propyl-2-methyl, 2-chloro-4-methyl, 3,4-diethoxy, 3-cyano-4-ethoxy-phenyl. Practically speaking, the "substituted phenyl" group is limited to a total of ten carbon atoms, e.g., 4-isobutylphenyl.

"Substituted phenoxy" means lower alkyl, lower alkoxy, halogen, nitro and cyano subtituted phenoxy. There can be combinations of substituents such as 4-propyl-2-methyl, 2-chloro-4-methyl, 3,4-diethoxy, 3-cyano-4-ethoxy, and the like. The substituted phenoxy is limited to a total of ten carbon atoms, e.g., 4-isobutylphenoxy.

"Substituted thiophenoxy" means lower alkyl, lower alkoxy, halogen, nitro, and cyano substituted thiophenoxy. There can be combinations of substituents such as 4-propyl-2-methyl, 2-chloro-4-methyl, 3,4-diethoxy. The substituted thiophenoxy is limited to a total of ten carbon atoms, e.g., 4-isobutylthiophenoxy.

The novel disulfides of this reaction are generally prepared by reacting sulfur monochloride or sulfur-monobromide with a phosphoramide having the formula

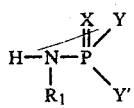
VI wherein Y and Y' are limited to the definitions of Y and Y' taken together to form a functionality selected from the group consisting of I', I'' and I''' as shown above.

Preparation of these disulfides is accomplished by treating a solution of a corresponding phosphoramide and a tertiary amine, such as triethylamine, with sulfur monochloride or sulfur monobromides. Solvents are acetonitrile and tetrahydrofuran, preferably acetonitrile. The temperature of the treatment is from $-20°$ to $+50°$ C., preferably 0° C. Cooling to about $-20°$, filtering and washing with water gives a good yield of high purity disulfides.

The invention is also directed to preparation of sulfenyl chlorides or bromides of phosphoramide solution prepared by a novel process. The process is recited above as step 1 in which a disulfide V is reacted with chlorine or bromine. The resulting sulfenyl halide compounds have the formula

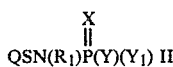  II wherein $R_1$, X, Y, and $Y_1$ are as defined above and Q is chlorine or bromine. Due to instability to these sulfenyl halides II when isolated complete physical and chemical data are difficult to obtain. However, NMR spectra and analysis of the pesticide made by reacting a sulfenyl chloride II with $ROC(O)N(CH_3)H$ in step 2 described above are both consistent with the conclusion that these compounds have formula II described herein.

Generally, step 1 and step 2 as set forth above are carried out in the following manner.

In step 1 a disulfide compound having the formula V in an inert solvent is reacted with chlorine or bromine. The solvent is any inert solvent, preferably acetonitrile, hexane, dichlormethane, or tetrahydrofuran. Although step 1 can be performed as an independent step, the step 1 solvent may preferably be one that can be used in the subsequent step 2 reaction as described herein. The chlorine may be added to the disulfide solution in the form of a gas and the bromine in the form of a liquid. Since the resulting chloro containing compounds are preferred, chlorine gas is the preferred cleveage agent for the disulfide in this reaction. This reaction may be carried out at temperatures from $-40°$ to $+25°$ C., preferably $-30°$ C. to $-10°$ C. However, when using chlorine gas the suggested temperature range is from $-30°$ to $+25°$ C., preferably from $-20°$ to $-10°$ C. The product resulting from this reaction may be used directly in the step 2 reaction described above if an appropriate solvent is present. Alternatively, the solvent useful in step 1 may be removed and substantially replaced by known methods with an appropriate solvent for the step 2 reaction. Preferred conditions for such replacement are low temperature and pressure in a nitrogen atmosphere.

In step 2 the sulfenyl halide product of step 1 is reacted with the amide compound. $ROC(O)N(CH_3)H$. The reaction is effected in the cold, preferably $-20°$ to $+25°$ C., in the presence of a suitable acid acceptor and an inert organic medium. Illustrative of suitable acid acceptors are trialkyl amine, (e.g., triethylamine) pyridine and lutidine. Illustrative of the organic media for the reaction are dimethylformamide, diethylether, hexane, tetrahydrofuran, methylene chloride and acetonitrile, the preferred media being tetrahydrofuran. Cuprous chloride and aluminum chloride may be used to catalyze the reaction. Cuprous chloride is the preferred catalyst.

The desired compounds according to Formula I are recovered and purified according to conventional methods. Filtration, solvent evaporation, chromatography, crystallization, and combinations thereof are employed. Some of the compounds are obtained as crystals while others are purified as oils.

This invention includes unexpected advantages over that known in the art. The advantages are shown above in the step 1 reaction with disulfides. The disulfide reaction with chlorine or bromine is novel and results in unexpectedly improved yields of the sulfenyl halides II. Therefore, improved yields of desired pesticides are obtained when compounds II are reacted with the compounds having the formula ROC(O)N(CH$_3$)H, as shown by step 2 above. In fact, yields indicate nearly a stoichiometric reaction between sulfenyl chlorides in the solution obtained in step 1 and the compound ROC-(O(N)CH$_3$)H in step 2. For comparision, the use of sulfur dichloride and sulfuryl chloride in analogous preparations of corresponding sulfenyl chlorides are disclosed in U.S. Pat. No. 4,081,536, U.S. Pat. No. 4,024,277, U.S. application Ser. No. 962,266, filed Nov. 20, 1978, and the Alimov, et al. references discussed above. The sulfenyl chloride in solution made by these prior art preparations reacts with only about one half the expected amount of compounds of formula ROC-(O)N(CH$_3$)H when used in a coupling step 2 reaction similar to that shown herein. Therefore, the process of step 1 in this invention is unexpectedly advantageous and unobvious.

Another disadvantage of one of the above noted prior art methods is that the desired pesticide decomposes in the presence of sulfur dichloride. In other words, if sulfur dichloride is used to make a sulfenyl chloride for use in the further reaction to the desired pesticide, intervening steps are required to thoroughly remove residual sulfur dichloride before proceeding to the further reaction.

Therefore, in summary it is now found that the generation of a product having the formula II noted above by a heretofore unknown reaction process shown in step 1 in which a compound having the formula V is reacted with chlorine or bromine and further coupling with a compound ROC(O)N(CH$_3$)H shown in step 2 is unexpectedly advantageous. For example, improved yields result. Furthermore, selected disulfides useful herein ae novel.

The following examples illustrate each novel aspect of this invention and at the same time demonstrate the total process for the preparation of a desired pesticide I. However, these examples should not be considered limiting as to the use of any particular part of the invention process.

Starting materials for use in the present invention are known, available or can be prepared by methods described in the prior art.

The definitions and explanations below are for the terms as used throughout the entire patent application including both the specification and claims.

g Refers to grams, Kg refers to kilograms, gal refers to gallons, mol refers to mole, ml refers to milliliter, l refers to liters, C refers to carbon, NMR refers to nuclear magnetic resonance, mp refers to melting point, mass spec. refers to mass spectrometry, mmol refers to millimole. TLC refers to thin-layer chromatography.

Preparation I:
N,N'-dithiobis[N-(1-methylethyl)-1,3,2-dioxaphosphorinan-2-amino]2,2'-disulfide V$_1$'

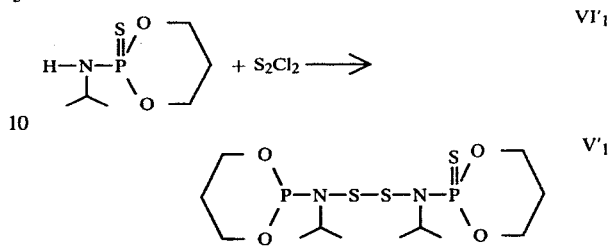

Phosphoramide VI$_1$' (19.0 g, 0.097 mol) and triethylamine (14.7 ml, 0.11 mol) are dissolved in tetrahydrofuran (50 ml) and cooled to 0° C. S$_2$Cl$_2$ (sulfur monochloride) (4.3 ml, 0.053 mol) in tetrahydrofuran (50 ml) is added over 40 minutes with stirring. The temperature reaches 5° C. during the addition and a voluminous white precipitate forms. After an additional 30 minutes, 200 ml of H$_2$O (water) is added and the solids are filtered. The filter cake is washed two times with 30 ml of water each time and one time with 50 ml of ice cold acetone to give a white powder which is dried in a vacuum oven at 60° C. for 10 hours. N,N'-dithiobis[N-(1-methylethyl)-1,3,2-dioxaphosphorinan-2-amine]2,2'-disulfide V$_1$' is obtained in the following yield: 17.4 g (80 percent); mp. 148.5–151. TLC: 25 percent ethyl acetate/hexane; R$_f$=0.16. Analytical data is:

NMR: δ=1.26 d, J=6.66 Hz (12H); 1.67–2.50 m (4H); 4.10–4.70 m (10H).

R$_f$: 60% ethylacetate/hexane—0.56.
R$_f$: 30% ethylacetate/hexane—0.18.
mp: 150–152 (acetone).
C and H: Calc. C, 31.85; H, 5.79; N, 6.19, P, 13.69; S, 28.34. Found: C, 31.94; H, 5.70; N, 6.19; P, 13.75; S, 28.28

Mass Spec: M+, 452; M-194, 258; M-226, 226; M-258, 194.

Preparation II:
N,N'-dithiobis[5,5-dimethyl-N-(1,1-dimethylethyl)-1,3,2-dioxaphosphorinan-2-amine], 2,2'-disulfide V'$_2$

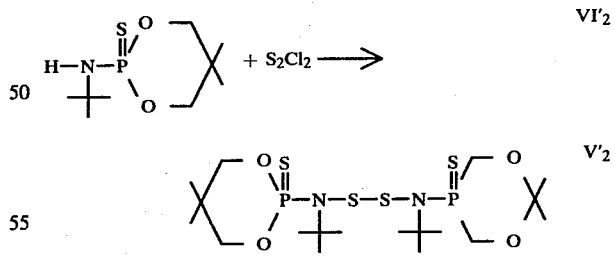

Phosphoramide VI$_2$' (161.9 Kg, 682 mol) and triethylamine (77.7 Kg, 769 mol) are dissolved in tetrahydrofuran (169.2 l) and cooled to 0° C. S$_2$Cl$_2$ (sulfur monochloride) (45.9 Kg, 340 mol) is added over 40 minutes with stirring. The temperature reaches 5° C. during the addition and a voluminous white precipitate forms. After an additional 30 minutes the temperature is reduced to −20° C. and the solids ae filtered. The filter cake is washed two times with 50 gal of water each time and one time with 20 gal. of ice cold acetonitrile to give a white powder which is dried in a vacuum oven at 45°

C. for 2 days. N,N'-dithiobis[5,5-dimethyl-N-(1,1-dimethylethyl)-1,3,2-dioxaphosphorinan-2-amine]2,2'-disulfide V'$_2$ is obtained in the following yield: 148 Kg (276 mol), 81 percent. Analytical data is summarized as follows: mp 152–154, TLC 20 percent ethylacetate/hexane R$_f$=0.6.

Appropriate phosphoramide VI starting materials are substituted in reactions similar to Preparation I and II according to the process as described herein to prepare corresponding novel intermediates V' of the invention as follows:

N,N'-dithiobis[5,5-diethyl-N-(1-methylethyl)-1,3,2-dioxaphosphorinan-2-amine], 2,2'-disulfides;

N,N'-dithiobis[5,5-dimethyl-N-ethyl-1,3,2-dioxaphosphorinan-2-amine], 2,2'-disulfide;

N,N'-dithiobis[N-(1-methylethyl)-1,3,2-dioxaphospholan-2-amine], 2,2'-disulfide;

N,N'-dithiobis[4,4,6-trimethyl-N-(1-methylethyl)-1,3,2-dioxaphosphorinan-2-amine], 2,2'-disulfide;

N,N'-dithiobis[5,5-diethyl-N-cyclohexyl-1,3,2-dioxaphosphorinan-2-amine], 2,2'-disulfide;

N,N'-dithiobis[5,5-dimethyl-N-cyclohexyl-1,3,2-dioxaphosphorinan-2-amine], 2,2'-disulfide;

N,N'-dithiobis[N-methyl-1,3,2-dioxaphosphorinan-2-amine], 2,2'-disulfide;

N,N'-dithiobis[hexahydro-N-cyclopentyl-1,3,2-benzodioxaphosphol-2-amine], 2,2'-disulfide;

N,N'-dithiobis[N-(2-methylpropyl)-1,3,2-benzodioxaphosphol-2-amine], 2,2'-disulfide.

Examples of the novel product or solution of the invention which is believed to contain sulfenyl chlorides II shown by step 1 above is illustrated by the following Examples A and B.

EXAMPLE A

N,N'-dithiobis[N-(1-methylethyl)-1,3,2-dioxaphosphorinan-2-amine], 2,2'-disulfide V$_1$' from Preparation 1 (3.09 g, 6.8 mmol) is stirred with dichloromethane (9 ml) and cooled to 0° C. Cl$_2$ (chlorine) gas is sparged into the suspension until TLC indicates complete consumption of disulfide. A mild exotherm occurs during the sparging with the final temperature reaching 5° C. The resulting yellow, homogeneous solution may be used directly or the dichloromethane can be replaced with tetrahydrofuran which is the preferred solvent of the subsequent step 2 reaction of the present invention.

The active compound resulting from Example A is [(1-methylethyl)(2-thio-1,3-dioxa-2-phosphocyclohex-2-yl)amine]sulfenyl chloride II$_1$.

EXAMPLE B

N,N'-dithiobis[5,5-dimethyl-N-(1,1-dimethylethyl) 1,3,2-dioxaphosphorinan-2-amine], 2,2'-disulfide V'$_2$ from Preparation II (400 mg, 0.745 mmol) is suspended in 2 ml carbon tetrachloride and cooled in an ice-methanol bath at −10°. Chlorine in carbon tetrachloride (1.82 M, 0.41 ml, 0.75 mmol) is added over three minutes during which time the mixture becomes homogeneous. The pmr spectrum of this solution shows significant changes from the spectrum of the disulfide. No significant change in the spectrum occurs on standing 16 hours at room temperature.

PMR (CDCl$_3$, TMS):

Disulfide—4.45–3.20 (M, 8H, —OCH$_2$), 1.56:

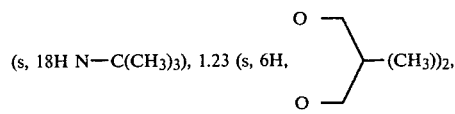

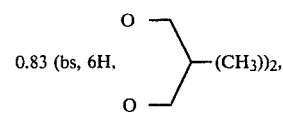

sulfenyl chloride - 4.10 (dd, 4H, O—CH$_2$), 1.66

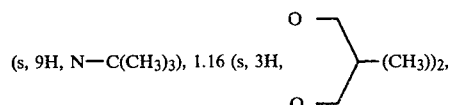

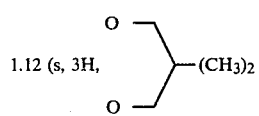

m=multiplet, s=singlet, bs=broad singlet, dd=doublet of doublets.

Thus, the active compound resulting from Example B is [1,1-dimethylethyl)(5,5-dimethyl 2-thio-1,3-dioxa-2-phosphocyclohex-2-yl)amino]sulfenyl chloride II'$_2$.

Appropriate disulfide V starting materials are substituted in Examples A and B according to the process as described herein to prepare corresponding novel products or solutions of the process. The disulfide V includes those selected novel compounds V' named above as well as other disulfides included in the above noted generic scope shown as step 1.

Likewise, other chlorine or bromine generating agents named herein are substituted for chlorine gas in Examples A and B according to the process as described herein to prepare similar chlorine or bromine containing products respectively.

Examples I and II provide experimental descriptions showing the above step 2 in which the desired pesticide I is obtained.

EXAMPLE I

Preparation of methyl N-[[[methyl[[(1-methylethyl)(2-thioxo-1,3,2-dioxaphosphorinan-2-yl)amino]thio]amino]carbonyl]oxy]ethanimidothioate, I$_1$'

A solution from Example A above (13.6 mmol) in dichloromethane (9 ml) is added to an emerald green colored solution of methyl-[[(methylamino)carbonyl]oxy]ethanimidothioate hereinafter named methomyl (2.05 g, 12.6 mmol) triethylamine (2.0 ml, 14.5 mmol) and CuCl (cuprous chloride) (0.062 g, 0.63 mmol) in tetrahydrofuran (15 ml) at 0° over five minutes. A precipitate develops and the reaction color changes to olive green. After 45 minutes the reaction is filtered and the filter cake (triethylamine hydrochloride plus product) is washed one time with hexane and three times with water. The white solid is dried 12 hours at 40° C. under vacuum to yield 2.0 g (40 percent) of product. The mother liquor contains another 1.1 g of product isolated by flash chromatography (60 percent ethyl acetate/hexane). The product yield is 62 percent; mp.

137-139 (low) of methyl N-[[[methyl[[(1-methylethyl)(2-thioxo-1,3,2-dioxaphosphorinan-2-yl)amino]thio]amino]carbonyl]oxy]ethanimidothioate I₁'.

In other words, the product generated by Example A above reacted in almost stoichiometric ratio with methomyl in tetrahydrofuran containing CuCl (cuprous chloride) (0.05 equiv.) and triethylamine to give 40 percent yield crystallized directly from the reaction mixture.

EXAMPLE II

Preparation of methyl N-[[[methyl[[(1,1-dimethylethyl)(5,5-dimethyl-2-thioxo-1,3,2-dioxaphosphorinan-2-yl)amino]thio]amino]-carbonyl]oxy]ethanimidothioate I₂'

A solution from Example B above (0.019 mmol) in tetrahydrofuran (25 ml) is added to an emerald green-colored solution of methomyl (2.3 g, 0.014 mol), triethylamine (2.8 ml, 0.020 mol) and CuCl (cuprous chloride) (0.071 g, 0.72 mmol) in tetrahydrofuran (5 ml) at 3° over five minutes. A precipitate develops and the reaction color changes to olive green. After 45 minutes the reaction is filtered and the filter cake (triethylamine hydrochloride plus product) is washed one time with cold tetrahydrofuran (20 ml) and three times with 30 ml of water. The white solid is dried 12 hours at 30° C. (under vacuum to yield 4.72 g) (76 percent) of the product N-[[[methyl[[(1,1-dimethylethyl)(5,5-dimethyl-2-thioxo-1,3,2-dioxaphosphorinan-2-yl)amino]thio]amino]carbonyl]oxy]ethanimidothioate I₂'., mp 163°-166° C.

Likewise, the product generated by Example B above reacted in almost stoichiometric ratio with methomyl in tetrahydrofuran containing CuCl (cuprous chloride and triethylamine).

Finally, appropriate products, prepared according to general processes as described herein in step 1 by substituting corresponding disulfides V in Examples A and B, are thereafter substituted in Examples I and II according to the process as described herein as step 2. Corresponding desired pesticides of formula I are thereby obtained.

For various reasons the chloro containing compounds resulting from cleaving the disulfide in step 1 may continue to be preferred (supra page 10). However, it is now found that a surprisingly greater yield of the desired compounds from step 2 is obtained from the novel bromo containing compounds resulting from cleaving the disulfide in step 1 with bromine.

Furthermore, this surprising increase in yield over the chloro containing compound makes the novel bromo containing sulfenyl halide product of step 1 also an unobvious invention.

The following comparison illustrates this novel aspect of the invention and at the same time again demonstrates the total process for the preparation of a desired pesticide I.

EXAMPLE III

Preparation of methyl N-[[[methyl[[(1,1-dimethylethyl)(5,5-dimethyl-2-thioxo-1,3,2-dioxaphosphorinan-2-yl)amino]thio]amino]-carbonyl]oxy]ethanimidothioate I₂'

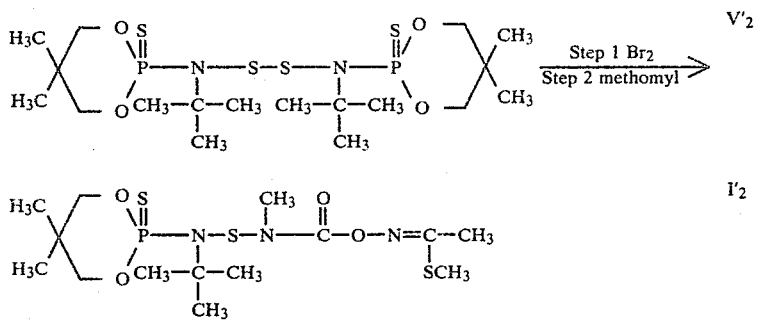

Elemental bromine (16.0 g, 0.100 mol) is added to a suspension of disulfide from Preparation II (53.6 g, 0.10 mol) in tetrahydrofuran (200 ml) over 5 minutes with cooling to maintain a reaction temperature of 5° to 10° C. After the addition the resultant deep orange solution containing the novel product [1,1-dimethylethyl(5,5-dimethyl-2-thio-1,3-dioxa-2-phosphacyclohex-2-yl)amino]sulfenyl bromide II₃' is stirred for 15 minutes and then added over 20 minutes to a solution of methyl N-[[(methylamino)carbonyl]oxy]ethanimidothioate (32.4 g, 0.200 mol), triethylamine (20.2 g, 0.20 mol) and cuprous chloride (0.35 g) in tetrahydrofuran (300 ml) while maintaining a reaction temperature of −10° to −15° C. After the addition the mixture is stirred for 90 minutes at −12°, then diluted with 500 ml of hexane. The precipitate is filtered and washed with two 200 ml portions of 1 to 1 methanol-water and dried at 40° in a vacuum oven to give 67.8 g (79%) of methyl N-[[[methyl[[(1,1-dimethylethyl)(5,5-dimethyl-2-thioxo-1,3,2-dioxaphosphorinan-2-yl)amino]thio]amino]carbonyl]oxy]ethanimidothioate I₂'. Analysis of this product by high performance liquid chromatography (HPLC) demonstrates a purity of 87.5%.

In an identical fashion but substituting chlorine (7.01 g, 0.100 mol) for bromine there is obtained 54.0 g, 63% of the above named product I' showing a purity by high performance liquid chromatography (HPLC) of 88.1%.

Comparison of the yields shows that the desired product is unexpectedly better from the process using bromine as cleaving agent for the disulfide rather than the previously exemplified process using chlorine.

The novel active compound resulting from step 1 above is [(1,1-dimethylethyl)(5,5-dimethyl-2-thio-1,3-dioxa-2-phosphacyclohex-2-yl)amino]sulfenyl bromide II₃'.

Appropriate disulfide V starting materials are substituted in a process similar to that of Example III wherein step 1 described herein is used to prepare corresponding novel bromides II. Such novel bromides include but are not limited to the following:

1. O,O-diethyl N-(bromothio)-N-(n-propyl)-phosphoramidothioate;

2. O,O-diethyl N-(bromothio)-N-phenyl-phosphoramidothioate;
3. O,O-diethyl N-(bromothio)-N-(i-propyl)-phosphoramidothioate;
4. O,O-dimethyl N-(bromothio)-N-methyl-phosphoramidothioate;
5. O,O-dimethyl N-(bromothio)-N-(i-propyl)-phosphoramidothioate;
6. O,O-dimethyl N-(bromothio)-N-(n-butyl)-phosphoramidothioate;
7. O,O-diethyl N-(bromothio)-N-methyl-phosphoramidothioate;
8. O,O-diethyl N-(bromothio)-N-methyl-phosphoramidate;
9. O,S-dimethyl N-(bromothio)-N-methyl-phosphoramidothioate;
10. O-methyl N-(bromothio)-N-(i-propyl)-P-phenylphosphonamidothioate;
11. O-methyl N-(bromothio)-N-methyl-P-phenylphosphonamidothioate;
12. O-methyl N-(bromothio)-N-methyl-P-methylphosphonamidothioate;
13. O-(i-propyl) N-(bromothio)-N-(i-propyl)-P-phenylphosphonamidothioate;
14. O-phenyl N-(bromothio)-N-methyl-P-methylphosphonamidothioate;
15. O-(i-propyl) N-(bromothio)-N-(i-propyl)-P-methylphosphonamidothioate;
16. O-methyl N-(bromothio)-N-(i-propyl)-P-methylphosphonamidothioate;
17. O-phenyl N-(bromothio)-N-(i-propyl)-P-methylphosphonamidothioate;
18. O-(4-chlorophenyl) N-(bromothio)-N-(i-propyl)-P-ethylphosphonamidothioate;
19. O-(4-phenylphenyl) N-(bromothio)-N-(i-propyl)-P-ethylphosphonamidothioate;
20. O-phenyl N-(bromothio)-N-ethyl-P-phenylphosphonamidothioate;
21. O-phenyl N-(bromothio)-N-phenylmethyl-P-ethylphosphonamidothioate;
22. O-phenyl N-(bromothio)-N-(n-butyl)-P-ethylphosphonamidothioate;
23. O,O-di-n-propyl N-(bromothio)-N-methylphosphoramidate;
24. O,O-di-n-propyl N-(bromothio)-N-(n-propyl)-phosphoramidate;
25. O,O-diethyl N-(bromothio)-N-(n-propyl)-phosphoramidate;
26. O,O-dimethyl N-(bromothio)-N-ethyl-phosphoramidate;
27. O,O-di-i-propyl N-(bromothio)-N-methyl-phosphoramidate;
28. O,O-diethyl N-(bromothio)-N-ethyl-phosphoramidate;
29. O,O-diphenyl N-(bromothio)-N-methyl-phosphoramidate;
30. O,O-diphenyl N-(bromothio)-N-(2-phenylethyl)-phosphoramidate;
31. O-i-propyl N-(bromothio)-N-phenyl-P-methylphosphonamidothioate;
32. O-phenyl N-(bromothio)-N-benzyl-P-ethylphosphonamidothioate;
33. O-phenyl N-(bromothio)-N-(4-chlorophenyl)-P-ethylphosphonamidothioate;
34. O-ethyl N-(bromothio)-N-benzyl-P-phenylphosphonamidothioate;
35. O-(2-chlorophenyl) N-(bromothio)-N-phenyl-P-ethylphosphonamidothioate;
36. O-(4-chlorophenyl) N-(bromothio)-N-phenyl-P-ethylphosphonamidothioate;
37. O-phenyl N-(bromothio)-N-cyclohexyl-P-ethylphosphonamidothioate;
38. 2-[N-(bromothio)-N-(i-propyl)-amino]-5,5-dimethyl-2-thioxo-1,3,2-dioxaphosphorinane;
39. 2-[N-(bromothio)-N-(t-butyl)-amino]-5,5-dimethyl-2-thioxo-1,3,2-dioxaphosphorinane;
40. 2-[N-(bromothio)-N-(i-propyl)amino]-5,5-diethyl-2-thioxo-1,3,2-dioxaphosphorinane;
41. 2-[N-(bromothio)-N-ethylamino]-5,5-dimethyl-2-thioxo-1,3,2-dioxaphosphorinane;
42. 2-[N-(bromothio)-N-(i-propyl)amino]-2-thioxo-1,3,2-dioxaphospholane;
43. 2-[N-(bromothio)-N-(i-propyl)amino]-2-thioxo-1,3,2-dioxaphosphorinane;
44. 2-[N-(bromothio)-N-(ethyl)amino]-2-thioxo-1,3,2-dioxaphosphorinane;
45. 2-[N-(bromothio)-N-cyclohexylamino]-5,5-diethyl-2-thioxo-1,3,2-dioxaphosphorinane;
46. 2-[N-(bromothio)-N-cyclohexylamino]-5,5-dimethyl-2-thioxo-1,3,2-dioxaphosphorinane;
47. 2-[N-(bromothio)-N-methylamido]-2-thioxo-1,3,2-dioxaphosphorinane;
48. 2-[N-(bromothio)-N-cyclopentylamino]-2-oxo-3a,4,5,6,7,7a-hexahydro-2-oxo-1,3,2-benzodioxaphosphole;
49. 2-[N-(bromothio)-N-(i-propyl)amino]-2-thioxo-1,3,2-benzodioxaphosphole;
50. 2-[N-(bromothio)-N-cyclohexylamino]-5,5-dimethyl-2-oxo-1,3,2-dioxaphosphorinane;
51. 2-[N-(bromothio)-N-(i-propyl)amino]-2-oxo-1,3,2-dioxaphosphorinane;
52. 2-[N-(bromothio)-N-(t-butyl)amino]-5,5-dimethyl-2-oxo-1,3,2-phosphorinane;
53. 2-[N-(bromothio)-N-(3,4-dimethylphenyl)amino]-5,5-dimethyl-2-oxo-1,3,2-phosphorinane; and
54. 2-[N-(bromothio)-N-benzylamino]-2-thioxo-1,3,2-phosphorinane.
55. 2-[N-(bromothio)-N-(methyl)amino]-5,5-dimethyl-2-thioxo-1,3,2-dioxaphosphorinane,
56. 2-[N-(bromothio)-N-(n-butyl)amino]-5,5-dimethyl-2-thioxo-1,3,2-dioxaphosphorinane,
57. 2-[N-(bromothio)-N-(phenyl)amino]-5,5-dimethyl-2-thioxo-1,3,2-dioxaphosphorinane,
58. 2-[N-(bromothio)-N-(t-butyl)amino]-5,5-dimethyl-2-thioxo-1,3,2-dioxaphosphorinane,
59. 2-[N-(bromothio)-N-(methyl)amino]-5,5-dimethyl-2-oxo-1,3,2-dioxaphosphorinane,
60. 2-[N-(bromothio)-N-(ethyl)amino]-5,5,-dimethyl-2-oxo-1,3,2-dioxaphosphorinane,
61. 2-[N-(bromothio)-N-(i-propyl)amino]-5,5-dimethyl-2-oxo-1,3,2-dioxaphosphorinane,
62. 2-[N-(bromothio)-N-(n-butyl)amino]-5,5-dimethyl-2-oxo-1,3,2-dioxaphosphorinane,
63. 2-[N-(bromothio)-N-(methyl)amino]-1,3,2-dioxaphospholane,
64. 2-[N-(bromothio)-N-(t-butyl)amino]-2-thioxo-1,3,2-dioxaphospholane,
65. 2-[N-(bromothio)-N-(n-butyl)amino]-4-methyl-2-oxo-1,3,2-dioxaphospholane,
66. 2-[N-(bromothio)-N-(phenyl)amino]-4-methyl-2-oxo-1,3,2-dioxaphospholane,
67. 2-[N-(bromothio)-N-(1,1-dimethylpropyl)amino]-4-methyl-2-oxo-1,3,2-dioxaphospholane,
68. 2-[N-(bromothio)-N-(t-butyl)amino]-2-thioxo-1,3,2-dioxaphosphorinane, 69. 2-[N-(bromothio)-N-(3,4-dimethylphenyl)amino]-2-thioxo-1,3,2-dioxaphosphorinane,
70. 2-[N-(bromothio)-N-(n-butyl)amino]-2-oxo-1,3,2-dioxaphosphorinane,
71. 2-[N-(bromothio)-N-(i-propyl)amino]-2-oxo-1,3,2-dioxaphosphorinane,
72. 2-[N-(bromothio)-N-(i-butyl)amino]-2-oxo-1,3,2-dioxaphosphorinane,
73. 2-[N-(bromothio)-N-(methyl)amino]-5,5-diethyl-2-thioxo-1,3,2-dioxaphosphorinane,
74. 2-[N-(bromothio-N-(4-chlorophenyl)amino]-5,5-diethyl-2-thioxo-1,3,2-dioxaphosphorinane,
75. 2-[N-(bromothio)-N-(ethyl)amino]-2-thioxo-4,4,b-trimethyl-1,3,2-dioxaphosphorinane,
76. 2-[N-(bromothio)-N-(2-propyl)amino]-2-thioxo-4,4,b-trimethyl-1,3,2-dioxaphosphorinane,
77. 2-[N-(bromothio)-N-(2,2-dimethylpropyl)amino]-2-thioxo-1,3,2-dioxaphosphorinane,
78. 2-[N-(bromothio)-N-(i-propyl)amino]-5,5-diethyl-2-oxo-1,3,2-dioxaphosphorinane,
79. 2-[N-(bromothio)-N-(t-butyl)amino]-5,5-diethyl-2-oxo-1,3,2-dioxaphosphorinane.

Likewise, appropriate final products, prepared from the novel bromides are obtained by substituting each bromide from the preparations of step 1 above in step 2.

I claim:
1. A process for preparing a compound having the formula:

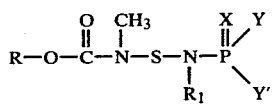   I wherein R is selected from the group consisting of

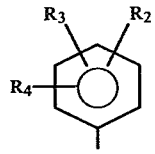   a.

wherein $R_2$, $R_3$, and $R_4$ are the same or different and are selected from the group consisting of hydrogen, lower alkyl of one to five carbon atoms, inclusive, halogen, lower alkoxy of one to five carbon atoms, inclusive, lower alkylthio of one to five carbon atoms, inclusive, dialkylamino with each alkyl the same or different and having one to three carbon atoms, inclusive, and $N=CHN(CH_3)_2$;

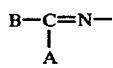   B.

wherein A and B are the same or different and are selected from the group consisting of lower alkyl of one to five carbon atoms, inclusive, lower alkylthio of one to five carbon atoms, inclusive, phenylthio wherein phenyl is unsubstituted or substituted with one to three substituents, same or different, selected from the group consisting of halogen and lower alkyl of one to four carbon atoms, inclusive, monocyano substituted alkylthio of one to five carbon atoms, inclusive, cyano, alkoxy having one to five carbon atoms, inclusive, phenyl, and hydrogen, with the proviso that when A is hydrogen, B is of the formula:

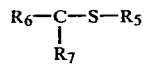

wherein $R_5$ is selected from the group consisting of alkyl of one to three carbon atoms, inclusive, and phenyl; $R_6$ is alkyl of one to three carbon atoms, inclusive, $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula:

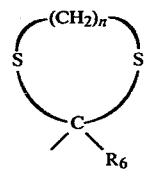

wherein n is 2 or 3 and the alkylene portion of the ring is unsubstituted or substituted with one or two methyl groups; A and B taken together with the carbon atoms to which they are attached form a dithio heterocyclic of the formula:

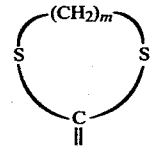

wherein m is 2 or 3 and the alkylene portion of the ring is unsubstituted or substituted with one to two methyl groups, and

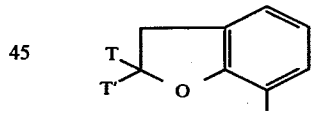   c.

wherein T and T' can be the same or different and are selected from the group consisting of hydrogen and lower alkyl of from one to six carbons; $R_1$ is selected from the group consisting of lower alkyl, phenyl, substituted phenyl, phenyl lower alkyl, and cyclo alkyl; X is oxygen or sulfur; Y and Y' are taken together to form a functionality selected from the group consisting of:

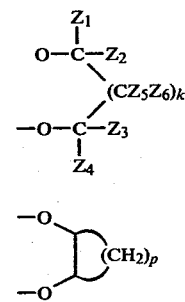

and

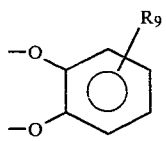 I'''

$Z_1$ through $Z_6$ are the same or different and are selected from the group consisting of hydrogen, methyl and ethyl, and k is 0 or 1; p is three or four, and $R_9$ is selected from the group consisting of hydrogen, lower alkyl, lower alkoxy and halogen; which comprises (1) contacting a compound having the formula:

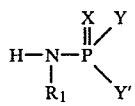 VI with the sulfur monochloride or sulfur monobromide, wherein $R_1$, X, Y and Y' are as defined above; (2) contacting the product of step 1 having the formula

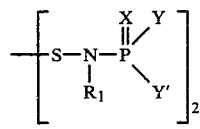 V with chlorine or bromine, and (3) contacting the product of step 2 with a compound having the formula

ROC(O)N(CH₃)H, wherein R is the same as above.

2. A process for preparing a compound having the formula:

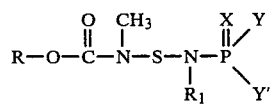 I wherein R is selected from the group consisting of:

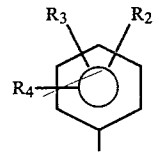 a.

wherein $R_2$, $R_3$, and $R_4$ are the same or different and are selected from the group consisting of hydrogen, lower alkyl of one to five carbon atoms, inclusive, halogen, lower alkoxy of one to five carbon atoms, inclusive, lower alkylthio of one to five carbon atoms, inclusive, dialkylamino with each alkyl the same or different and having one to three carbon atoms, inclusive, and N=CHN(CH₃)₂;

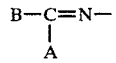 b.

wherein A and B are the same or different and are selected from the group consisting of lower alkyl of one to five carbon atoms, inclusive, lower alkylthio of one to five carbon atoms, inclusive, phenylthio wherein phenyl is unsubstituted or substituted with one to three substituents, same or different, selected from the group consisting of halogen and lower alkyl of one to four carbon atoms, inclusive, monocyano substituted alkylthio of one to five carbon atoms, inclusive, cyano, alkoxy having one to five carbon atoms, inclusive, phenyl, and hydrogen, with the proviso that when A is hydrogen, B is of the formula:

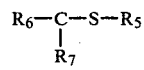

wherein $R_5$ is selected from the group consisting of alkyl of one to three carbon atoms, inclusive, and phenyl; $R_6$ is alkyl of one to three carbon atoms, inclusive; $R_7$ is selected from the group consisting of alkyl of one to three carbon atoms, inclusive, and $SR_8$, wherein $R_8$ is alkyl and is the same alkyl group as $R_5$, and taking $R_5$ and $R_8$ together with the atoms to which they are attached form a dithio heterocyclic of the formula:

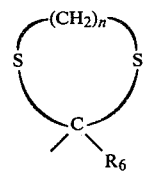

wherein n is 2 or 3 and the alkylene portion of the ring is unsubstituted or substituted with one or two methyl groups; A and B taken together with the carbon atoms to which they are attached form a dithio heterocyclic of the formula:

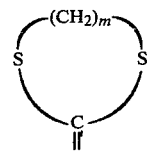

wherein m is 2 or 3 and the alkylene portion of the ring is unsubstituted or substituted with one to two methyl groups; and

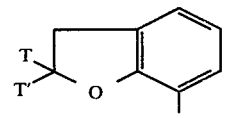 c.

wherein T and T' can be the same or different and are selected from the group consisting of hydrogen and lower alkyl of from one to six carbons; $R_1$ is selected from the group consisting of lower alkyl, phenyl, substituted phenyl, phenyl lower alkyl, and cyclo alkyl; X is oxygen or sulfur; Y and Y' are taken together to form a functionality selected from the group consisting of:

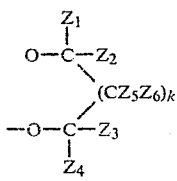 I'

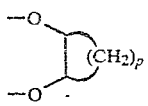 I"

and

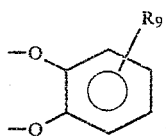 I'''

$Z_1$ through $Z_6$ are the same or different and are selected from the group consisting of hydrogen, methyl and ethyl, and k is 0 or 1; p is three or four, and $R_9$ is selected from the group consisting of hydrogen, lower alkyl, lower alkoxy and halogen; which comprises (1) contacting a compound having the formula

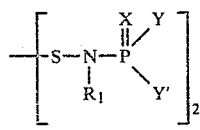 V wherein $R_1$, X, Y, and Y' are as defined above in a solvent with chlorine or bromine and (2) reacting the product of step (1) with a compound having the formula ROC(O)N(CH$_3$)H, wherein R is the same as above.

3. The process according to claim 2 or 1 wherein the compound having the formula

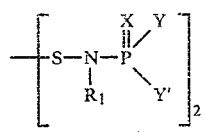 V wherein $R_1$, X, Y and Y' are as defined for formula I is contacted with chlorine.

4. A process according to claim 3 wherein the chlorine is chlorine gas.

5. The process according to claim 4 for preparing the compound methyl N-[[[methyl[[(1-methylethyl)(2-thioxo-1,3,2,-dioxaphosphorinan-2-yl)amino]thio]amino]carbonyl]oxy]ethanimidothioate.

6. A process according to claim 4 for preparing the compound methyl N-[[[methyl[[(1,1-dimethylethyl)(5,5-dimethyl-2-thioxo-1,3,2-dioxaphosphorinan-2-yl)amino]thio]amino]carbonyl]oxy]ethanimidothioate.

7. A process according to claim 2 or 1 wherein the compound having the formula

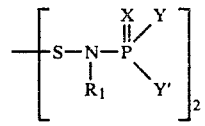 V wherein $R_1$, X, Y and Y' are as defined for formula I is contacted with bromine.

8. A process according to claim 7 for preparing a compound methyl N-[[[methyl[[(1-methylethyl)(2-thioxo-1,3,2-dioxaphosphorinan-2-yl)amino]thio]amino]carbonyl]oxy]ethanimidothioate.

9. A process according to claim 7 for preparing the compound methyl N-[[[methyl[[(1,1-dimethylethyl)(5,5-dimethyl-2-thioxo-1,3,2-dioxaphosphorinan-2-yl)amino]thio]amino]carbonyl]oxy]ethanimidothioate.

10. A process according to claim 2 wherein the reaction temperature of step 1 is maintaned between −30° and 25° C.

11. A process according to claim 2 wherein the solvent in step 1 is acetonitrile, hexane, dichloromethane, or tetrahydrofuran.

12. A process according to claim 11 wherein the solvent is tetrahydrofuran.

13. A process for preparing a compound having the formula:

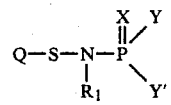 II wherein Q is selected from the group consisting of chlorine or bromine; $R_1$ is selected from the group consisting of lower alkyl, phenyl, substituted phenyl, phenyl lower alkyl, and cyclo alkyl; X is oxygen or sulfur; Y and Y' are taken together to form a functionality selected from the group consisting of:

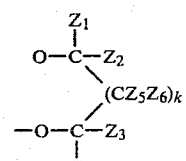 I'

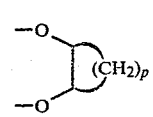 I"

and

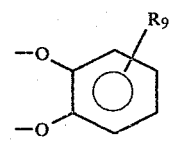 I'''

$Z_1$ through $Z_6$ are the same or different and are selected from the group consisting of hydrogen, methyl, and ethyl, and k is 0 or 1; p is three or four, and $R_9$ is selected from the group consisting of hydrogen, lower alkyl, lower alkoxy, and halogen which comprises reacting a compound selected from the group consisting of:

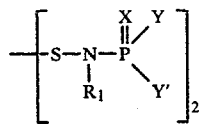

wherein X, R₁, Y and Y₁ are the same as above in a solvent with chlorine or bromine.

14. A process according to claim 13 wherein formula V is reacted with chlorine.

15. A process according to claim 14 wherein the chlorine is chlorine gas.

16. A process according to claim 13 wherein formula V is reacted with bromine.

17. A process according to claim 15 wherein the reaction temperature is maintained between −30° to 25° C.

18. A process according to claim 13 wherein the solvent is acetonitrile, hexane, dichloromethane, or tetrahydrofuran.

19. A process according to claim 18 wherein the solvent is tetrahydrofuran.

20. A process according to claim 15 for preparing the compound [(1-methylethyl)(2-thio-1,3-dioxa-2-phosphacyclohex-2-yl)amino]sulfenyl chloride.

21. A process according to claim 15 for preparing the compound [(1,1-dimethylethyl)(5,5-dimethyl-2-thio-1,3-dioxa-2-phosphacyclohex-2-yl)-amino]sulfenyl chloride.

22. A process according to claim 16 for preparing the compound [(1,1-dimethylethyl)(5,5-dimethyl-2-thio-1,3-dioxa-2-phosphacyclohex-2-yl)-amino]sulfenyl bromide.

* * * * *